(12) United States Patent
Piombini et al.

(10) Patent No.: US 8,117,899 B2
(45) Date of Patent: Feb. 21, 2012

(54) METHOD AND DEVICE FOR MEASURING THE GAS PERMEABILITY THROUGH FILMS AND WALLS OF CONTAINERS

(75) Inventors: Alessandro Piombini, Porto Azzuro (IT); Mauro Lucchesi, Lucca (IT)

(73) Assignee: Extrasolution S.R.L., Pisa (IT)

( * ) Notice: Subject to any disclaimer, the term of this patent is extended or adjusted under 35 U.S.C. 154(b) by 446 days.

(21) Appl. No.: 12/441,600

(22) PCT Filed: Sep. 14, 2007

(86) PCT No.: PCT/IB2007/002675
§ 371 (c)(1),
(2), (4) Date: Mar. 17, 2009

(87) PCT Pub. No.: WO2008/035159
PCT Pub. Date: Mar. 27, 2008

(65) Prior Publication Data
US 2009/0320564 A1 Dec. 31, 2009

(30) Foreign Application Priority Data

Sep. 19, 2006 (IT) .................................. PI2006A0108

(51) Int. Cl.
*G01N 15/08* (2006.01)
(52) U.S. Cl. .......................................................... 73/38
(58) Field of Classification Search .......................... None
See application file for complete search history.

(56) References Cited

U.S. PATENT DOCUMENTS

| | | | |
|---|---|---|---|
| 3,604,246 A * | 9/1971 | Toren | 73/38 |
| 4,112,739 A | 9/1978 | Lyssy | |
| 4,391,128 A | 7/1983 | McWhorter | |
| 4,656,865 A | 4/1987 | Callan | |
| 4,852,389 A * | 8/1989 | Mayer et al. | 73/38 |
| 2002/0162384 A1 | 11/2002 | Sharp | |
| 2009/0282900 A1 * | 11/2009 | Piombini et al. | 73/38 |

OTHER PUBLICATIONS

R.W. Balluffi, S.M. Allen, W.C. Carter, "Kinetics of Materials", Dec. 30, 2005, John Wiley & Sons, Hoboken, New Jersey, USA; XP002468865, p. 99-103.

* cited by examiner

*Primary Examiner* — Harshad Patel
(74) *Attorney, Agent, or Firm* — Roylance, Abram, Berdo & Goodman, L.L.P.

(57) ABSTRACT

A device for measuring permeability of a gas sample through a thin film, or a wall, arranged as a membrane between a first chamber and a second chamber of a measurement cell is provided that includes, a pressure regulator, upstream from each inlet to the measurement cell, that are each associated with a respective pressure sensor. A humidifier can be used, if desired. The device further includes that can switch the flows of gas between a starting wash step and a measurement step. Each gas flow is adjusted at the exit of the respective flow regulator. A control unit operates the pressure regulators and flow regulators to keep at predetermined values the total pressure in the first chamber and second chamber with those values maintained equal to each other.

21 Claims, 4 Drawing Sheets

METHOD AND DEVICE FOR MEASURING THE GAS PERMEABILITY THROUGH FILMS AND WALLS OF CONTAINERS

FIELD OF THE INVENTION

The present invention relates to a sensing device of the permeability of a gas through the walls of containers, in general containers for industrial products, for example plastic film containers for food, chemical, pharmaceutical, electronic products, etc.

DESCRIPTION OF THE PRIOR ART

For preserving products, in particular food in a container, a plastic bag or a thin sheet/film wrapper, it is desirable to minimize the gas migration through the walls of the container. This way it is possible to protect the organoleptic properties of the products by preserving the gaseous mixture created inside the packaging of the products. To preserve the composition of this mixture with time it is necessary that the wrapper blocks or limits any gas migration, not only through possible closure parts or welding zones, but also through the walls of the container.

A similar need is felt for other products, such as chemical and pharmaceutical products, electronic and optoelectronic devices and other articles that can be altered if in contact with the gaseous atmosphere present in the environment.

For determining the permeability of a film that can be used to make such containers a permeated gas flow through said film is measured. Systems are known to be adapted to carry out a gas flow measurement through a thin film or a wall. One of these is described in DE4142064 and comprises a measurement cell consisting of two shells facing at opposite sides with respect to a thin film sample of which permeability has to be determined; the thin film sample is placed between such shells, where such shells are sealed against the sample in order to create two chambers tightly separated by this film sample. Both chambers have an inlet and an outlet for a gas or a mixture of gas so that the gas flows in such chambers contacting at opposite sides the above described film. Owing to the permeability of the film, an amount of gas permeates from a chamber to the other so that for measuring the permeability of the film it is enough to measure the concentration of the permeated gas that reaches a sensor conveyed by a gas carrier at a known flow rate. This permeability (as given by the product of a diffusion coefficient and of a solubility coefficient that is typical for the specific material of the film as determined by known systems) is evaluated as the concentration of the gas permeating into the container in the gaseous carrier. This concentration increases with time, until reaching an asymptote parallel to the time axis of a concentration/time chart at this concentration, of the flow permeating through is the same as the flow into the chamber.

The above described known systems, however, have the drawback that they are slow. The concentration increases slowly with time which then requires a rather long time to stabilize before measurements are taken. In addition if the permeability features of different films have to be compared, the measurement time becomes very long indeed.

Another drawback of the known systems is that they provide very low intensity output signals. This is especially true for analysis of low permeability films. The result is an increase in the measurement time before a signal that can be obtained that is intense enough to be detected by common sensors.

SUMMARY OF THE INVENTION

In the following description, permeability is measured by the flow of the gas through the film or wall at steady state conditions. It is, therefore, an object of the present invention to provide a method and a device for measuring the permeability of a gas through a fraction of a thin film or of a wall that overcomes the above described drawbacks.

A particular object of the present invention is to provide a method and a device adapted to carry out a measurement of permeability of a gas through a film, in a way that is faster than the known systems.

Another feature of the invention is to provide a method and a device adapted to measure permeability of a gas through a film, capable of amplifying the detected permeability signal with respect to the known systems.

These and other objects are achieved by a method for measuring the permeability of a gas sample through a thin film or a wall, comprising the steps of:
- arranging said thin film or wall as a membrane between a first and said second chamber to seal said membrane therebetween, whereby, said membrane separates said first and second chamber;
- causing said gas sample to flow into said first chamber and causing a gaseous carrier to flow into said second chamber whereby a portion of said gas sample permeates through said membrane into said second chamber through said membrane and is conveyed away by said gaseous carrier;
- measuring the fraction of said gas sample that permeated into said second chamber and is present in the flow of said gas carrier exiting from said second chamber;
- characterised in that said steps of causing said gas sample and said gas carrier to flow are made at a total pressure, of said gas sample and gas carrier in said first and second chamber, being of a predetermined value that is substantially larger than the pressure of the environment, the total pressure difference between said first and second chamber remaining substantially equal to zero.

In other words, even if the film is balanced having the a same pressure in the first and second chamber, the partial pressure of the gas permeating from the first chamber to the second chamber is increased, in order to control as desired the flow thereof through the membrane.

Preferably, the predetermined value of the total gas preserve is set between 2 and 15 bar and, preferably, between 3 and 7 bar. Advantageously, a further step is provided of reducing the total pressures in each of said first and second chamber up to a value less than said predetermined value. In particular, said lower value is selected from:
- a value less than said first predetermined value but higher than the atmospheric pressure;
- a value substantially equal to the atmospheric pressure.

According to the invention, by causing the gas sample and gas carrier to flow with a pressure more than atmospheric and with the total pressure in the first chamber always substantially equal to the total pressure of the second chamber, the permeated gas flow is higher than that in the prior art. Because the permeated gas flow rate is higher, a shorter transient phase is obtained (if a consequent variation of permeated flow is considered). Furthermore, since the permeated gas amount is higher, it is possible to use sensors that, in general, are less sensitive and less expensive.

In particular, the step of reducing the total pressure is obtained as desired by means of:

a feedback-type automatic control that controls the concentration of the gas and the total pressure in each of the first and second chambers; or a open loop-type automatic control unit that is programmed to control gas pressures in said first and second chambers.

Advantageously, the present invention provides a cleaning step for the of said first and second chambers and of the membrane. A controlled flow of carrier gas through said first and second chambers, the total pressure difference between said first and second chambers being kept at substantially equal to zero, the total pressure is increased up to a predetermined washing value that is preferably larger than the pressure of the environment.

According to another aspect of the invention, the above described objects are also fulfilled by a device for measuring the permeability of a gas through a membrane, such as a thin film or wall, the device comprising:

a first chamber and a second chamber having, respectively, a first opening and a second opening operatively facing to each other and arranged on opposite sides of a membrane between them, said first opening and said second opening being seal coupled with the external surfaces of said membrane, said first chamber and said second chamber having at least one respective inlet and a respective outlet, whereby a gas sample can flow into and out of said first chamber and whereby a carrier gas can flow into and out of said second chamber so that a fraction of said gas sample permeates through said membrane into said second chamber and flows with said carrier gas towards said outlet of said second chamber;

means for measuring and adjusting the flow in said first and second chamber;

means for measuring the concentration of the gas exiting from said second chamber;

characterised in that means are provided for measuring and adjusting the pressure in said first chamber and second chamber that increase the total pressure of said gas sample and gas carrier in the first and second chambers at a predetermined value that is substantially larger than the pressure of the environment, the total pressure difference between said first and second chamber remaining substantially equal to zero.

Advantageously, said means for measuring and adjusting are adapted also to reduce said total pressure in said first and second chamber up to a further total pressure predetermined value, not higher than said predetermined value.

The device according to the invention is then capable of carrying out the method as above described, causing the total pressures of the gas in the first chamber and in the second chamber to increase beyond a predetermined value while ensuring that the membrane separating the two chambers is subject to same pressures on both its surfaces, and not deformed. Advantageously, said device comprises a an automatic control unit adapted to control said means for adjusting the flows of said gas sample and carrier gas and said means for adjusting the total pressure of the gas in said first chamber and in said second chamber, in order to bring said total pressure beyond a predetermined value and so that said total pressure in said first chamber remains substantially equal to the total pressure in said second chamber.

Advantageously, the first chamber is in a first hollow object and said second chamber is in a second hollow body, said second hollow body creating a base and said first hollow object creating a cover that operatively engages with said base, said membrane being arranged between said base and said cover.

In particular, the cover is operatively pressed on said base by means of stopping means that is preferably selected from:
at least one bracket;
at least one screw;
a screw threaded surface between said cover and said base;
a fixed joint; and
at least one element for engaging said cover to said base, coupled pivotally for rotation or coupled slidingly with respect to said base.

In particular, the first and second chambers in the first hollow object and the second hollow body, both have cylindrical shapes that are preferably made by milling.

Advantageously, the means for measuring and adjusting the total pressure of the gas in said first and second chamber are arranged upstream from said first and second chamber.

In a preferred embodiment, the means for adjusting the flow are arranged downstream of the first and second chambers.

Advantageously, the means for measuring the concentration of the gas exiting from the second chamber is arranged downstream of the second chamber.

Advantageously, the measuring device of the invention comprises means for adding humidity to said gas sample as inlet to said first chamber. In particular, said means for adding humidity comprises:

an outer reservoir containing a liquid comprising water, said reservoir having an inlet and an outlet for a flow of said gas sample through said reservoir;

at least one inlet duct arranged upstream from said reservoir and exiting into said inlet and at least one delivery duct arranged downstream of said reservoir, said delivery duct exiting into said first chamber.

In particular, the inlet duct of said reservoir comprises a valve adapted to switch the flow of the gas sample between the inlet duct of the reservoir and the inlet of the first chamber. This way it is possible to have two parallel inputs for gas sample: one for dry gas (as in normal conditions) and one for humidified gas that crosses the reservoir and exits from the first chamber. By combining the fraction of dry gas and humidified gas, the desired humidity is obtained.

Advantageously, the humidification device comprises means for measuring the humidity of said gas sample, said means being preferably arranged downstream of the outlet of the first chamber.

In particular, the gas sample which permeates from the first chamber to the said second chamber through said membrane is selected from:
oxygen; and
carbon dioxide.

In particular, the gaseous carrier that carries permeated sample gas towards the outlet of the second chamber is selected from:
nitrogen;
hydrogen;
helium; and
a mixture of said gases.

BRIEF DESCRIPTION OF THE DRAWINGS

The invention will be made clearer with the following description of some embodiments, exemplifying but not limitative, with reference to the attached drawings wherein.

DESCRIPTION OF THE PREFERRED EMBODIMENTS

In the following description an example will be illustrated of a method according to the invention for measuring the permeability of a gas sample through a membrane of thin film or a wall. This method is applicable for example, to containers of food products, drugs and, in general, for all the products that need to be preserved under vacuum or in the presence of a predetermined mixture of gas for proper preservations. In such cases it is necessary to know the gas permeability of the film wall of the container. Such method is obtained with a device shown in FIG. 1, comprising a measurement cell 1 of known type having a first hollow object 70 or cover and a second hollow body or body of base 30, in each of which is determined a milled circular chamber, respectively denominated first chamber 3 and second chamber 4. Closing the cover 70 on the body of base 30 with the interposing of the membrane 2, the two chambers are separated from the membrane, which is of thin material of which is to be measured the gas permeability. One example of such a measurement is the permeability of a packaging material to oxygen.

Figure 3:
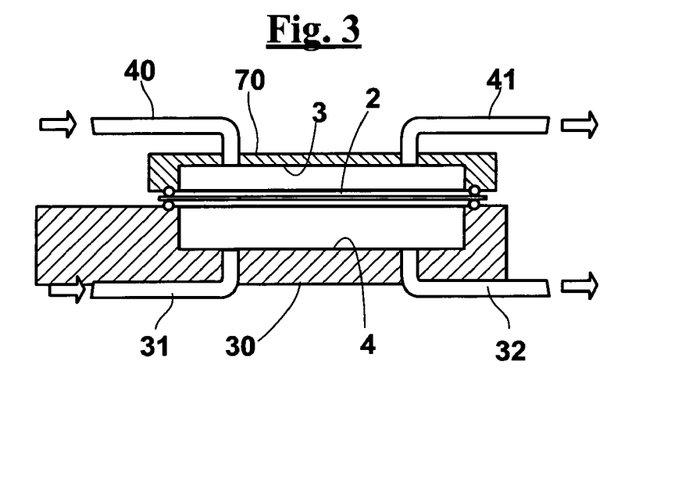
FIG. 3 shows a cross sectional view of a portion of a measuring device according to the invention.

Each of the two chambers 3 and 4, as shown in FIG. 3, has a respective inlet and an outlet for the flow of the gas. In particular, the first chamber 3 has an inlet 40 and an outlet 41 for a flow 25 of a sample gas, such as oxygen, to be used for measuring the permeability of membrane 2. Second chamber 4 has an inlet 31, through which is inserted a flow 26 of carrier gas, such as nitrogen, adjusted in pressure to match the total pressure of the first chamber so as not to stress membrane 2. The carrier gas flows towards outlet 32 and carries along sample gas that permeated into chamber 4 through membrane 2 during the measurements. Normally, the exit gas will include a flow 28 of nitrogen and oxygen.

Figure 1:
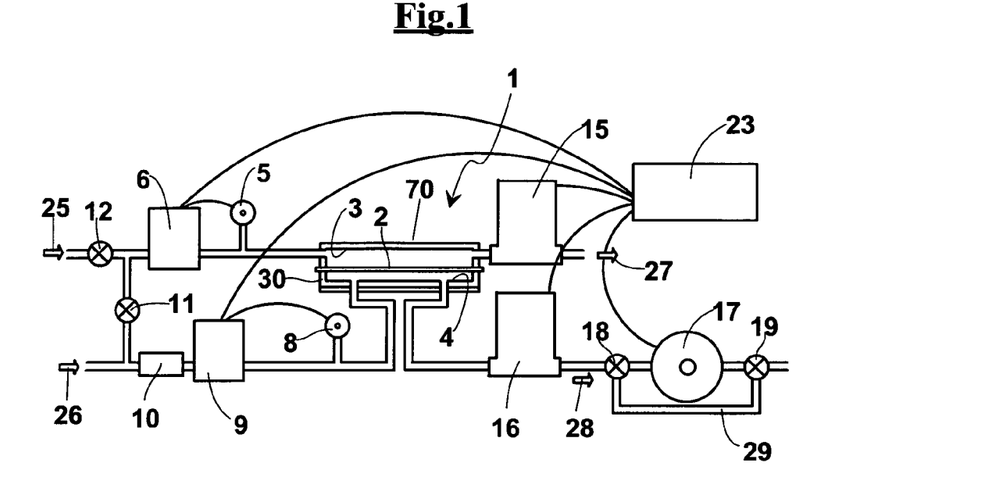
FIG. 1 shows a schematic view of a device according to the invention having a measurement cell for gas permeability through a thin film.

In FIG. 1, upstream from each inlet of the measurement cell 1, the device according to the invention comprises, for sample gas flow 25 and carrier gas flow 26, a pressure regulator 6, 9 associated with a pressure sensor 5, 8. For adding humidity to the carrier gas flow 26, the carrier gas flow 26 can be routed through inline 60 (FIG. 2), which comprises a water reservoir connected to a carrier gas outlet and inlet nipple in the body of base 30. The humidifier is preferably located immediately before the inlet 39 of carrier gas in cell 1. If desired, a second humidifier (not shown) can be used with sample gas flow 25. Catalyst 10 at the inlet of carrier gas flow 26 to capture and eliminate possible traces of oxygen that might be present in gaseous carrier.

The device comprises sealing valves 11 and 12 that can be used to switch the flows of gas between a preliminary cleaning step and an actual measurement process. In the cleaning step, a carrier gas, such as nitrogen is caused to flow into both the chambers 3 and 4 by opening only valve 11. During the actual measurement step, valve 11 is closed and valve 12 is opened to obtain two different flows of sample gas 25 and carrier gas 26.

Each gas flow is, moreover, adjusted with a flow regulator 15, 16 located downstream of chambers 3, 4. The carrier gas outlet flow 28 from chamber 4 is analysed by a sensor 17 that is specific for analysis of permeated sample gas. The valves 18 and 19, with the duct 29, allow sensor 17 to be by-passed by the carrier gas outlet flow.

A control unit 23, preferably of electronic type, operates the regulators of pressure 6 and 9 and of flow 15 and 18 in order to keep the total pressure in the first chamber 3 and in the second chamber 4 always substantially equal, both during the step of cleaning and during the measurement step. Equalized pressure on both sides avoids inbending or excessive mechanical stress on membrane 2. The measurement of the pressure in sample gas flow 25 and carrier gas flow 26 is by the pressure sensors 5 and 8.

Control unit 23 is also capable of recording the concentration of the sample gas, as determined by sensor 17, that permeated into the carrier gas through the membrane 2 thereby supplying an output value that represents the permeability of membrane 2.

The system of the present invention thus increases remarkably the partial pressure of the sample gas from the first chamber 3 that permeates into second chamber 4 while also maintaining a pressure equivalence or minimal pressure differential between the two chambers 3 and 4.

In particular, higher total pressures in first chamber 3 provides a higher permeation force from the sample gas into the second chamber 4 than prior systems thereby obtaining a higher concentration of the sample gas in the carrier gas for easier and more reliable measurements, as well as a shorter time to stabilization or equilibruim and final measurements as compared to known systems.

Figure 2:
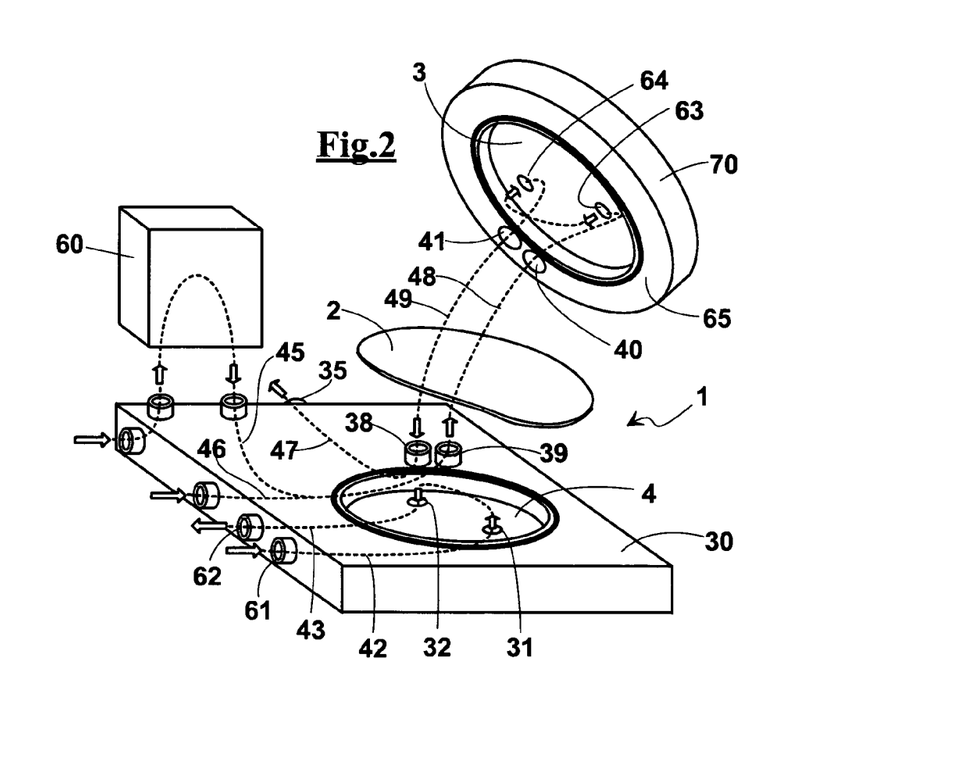
FIG. 2 shows an exploded view of a measuring device capable of carrying out the method according to the invention.

FIG. 2 shows a further embodiment of a device according to the invention which comprises a hollow body of base 30, a hollow body or cover 70, a humidifier that adds humidity to the flow of a carrier gas, a plurality of ducts for moving the gas. The chamber 4 in the body of base 30 has a hole inlet 31, for carrier gas (nitrogen), and a hole outlet 32 for the carrier gas and gas that has permeated through membrane 2, normally nitrogen plus oxygen. The holes 31 and 32 of second chamber 4 of base 30, communicate as indicated by dashed lines 42,43 with inlet ducts 61 and of discharge port 62 for the carrier and permeated sample gas. The inlet duct 61 is for carrier gas (such as nitrogen) and the discharge duct 62 containing the carrier gas and permeated sample gas (e.g., nitrogen and oxygen).

The cover 70 has a flange 65 that is superposed to the body of base 30. The chamber of the cover 3 has inlet holes 63 and outlet 64 of the gas of which is to be measuring the permeability through the membrane 2, communicating with relative inlet and outlet ducts made in the cover 70 leading to the holes 40 and 41 at the flange 65, which meet the respective fittings 39 and 38 on the base body 30 and communicating with relative further inlet ducts 46 and exhaust 47 that cross the base body 30, adapted to be crossed by carrier gas or sample gas.

For adding humidity to the inlet gas to the chamber 3 of the cover is provided a reservoir of water 60 out of the base body 30 and communicating with a duct 45 that goes in the inlet duct 46. It is therefore possible, having in parallel two inputs for carrier gas or sample gas, one for a dry gas or in normal conditions, and the other for the humidified gas that crosses the reservoir of water 60, falls within base body 30 and rejoins in the inlet duct 46. Combining the fraction of dry and wet gases it is possible to obtain the desired humidity. A humidity sensor is provided near the outlet channel 35.

The base body 30 is crossed by two ducts respectively inlet 42 and exhaust 43 of the gas in second chamber 4 in base 30, and two ducts respectively inlet 48 and exhaust 49 of the gas in first chamber 3 in cover 70.

It is possible then from the one hand to put the gas sample in first chamber 3 of cover 70 and let it out, following the path 48 and 49, giving to the gas a desired, controlled pressure, for example, atmospheric pressure and a measurable humidity. Furthermore, it is possible to allow neutral carrier gas to flow through second chamber 4 in the body of base 30 at atmospheric or at another, controlled pressure. The carrier gas, following the path 42 and 43, entrains the fraction of sample gas (oxygen) that has permeated into second chamber 4 of base 30 through membrane 2. A gas detector, not shown, that is located downstream of duct 43 is capable of giving the desired data of permeability.

A control panel, not shown, controls the incoming gas flows and from the outlets provides, data on the permeability of the membrane to the many sample gas that has permeated into second chamber 4.

A device according to the invention, described in FIGS. 1 and 2 and 3, carries out the method according to the invention. This method can comprise a first "cleaning" step of the membrane 2, during which the regulators of flow 15 and 16 let flow a controlled rate of carrier gas, typically nitrogen, into both the chambers 3 and 4, at a controlled pressure. This cleaning step purges gases trapped within thickness of membrane 2 and carries them away in the carrier gas. The first cleaning step is followed by a measurement sequence wherein a controlled amount of sample gas is allowed to flow into first chamber 3, whereas the effects of the permeation are recorded at the outlet of second chamber 4. This measurement step is done by adjusting the total pressures equally in both the first chambers 3 and second chamber 4, above a predetermined value. This increases the permeation of sample gas in second chamber 4 as well as its partial pressure thereby allowing a more accurate measurement of sample gas permeation rates in much less time than the known measurement systems. After the permeation process has started, the total pressures in chambers 3 and 4 can be reduced back to the standard conditions of 1 bar. The pressure reduction can be carried out with control of either the feedback on the signal produced by the permeated sample gas or on the pressure, or by a programmed delay time of the pressure regulator 6,9.

Figure 4:
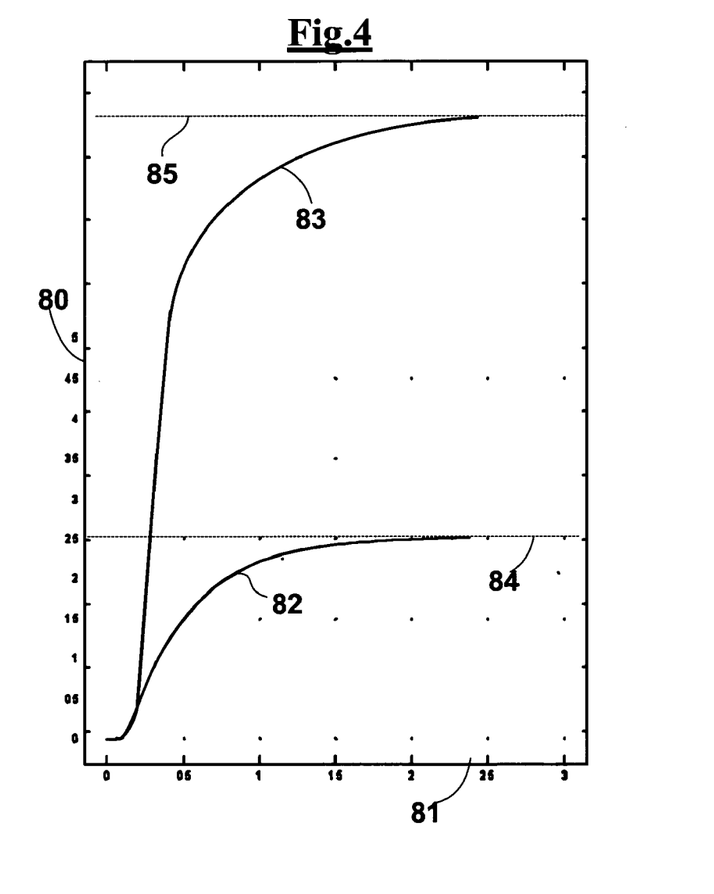
FIG. 4 shows a comparative diagram of the course of gas permeation versus time between the known devices and the device according to the invention, where the permeation measurement is carried out at a high pressure above atmospheric pressure.

FIG. 4 is a graph of permeation (y axis) versus time (x axis). The axis of the ordinate 80 is the permeate amount. The axis of the abscissa 81 is the time. In particular, prior art curve 82 represents the permeation course from the prior art techniques known, whereas permeation curve 83 represents the permeation course obtained with the present method. In particular, curve 83 measures high values of total pressure, in the first and second chambers, for example, a pressure equal to triple the maximum pressure that was used in the prior art. As is visible in FIG. 4, the permeation curve 83 assumed a larger value than the prior art curve 82 and reached a higher horizontal asymptote 85 than prior art asymptote 84. This technique can be useful in case of film with low permeability.

Figure 5:
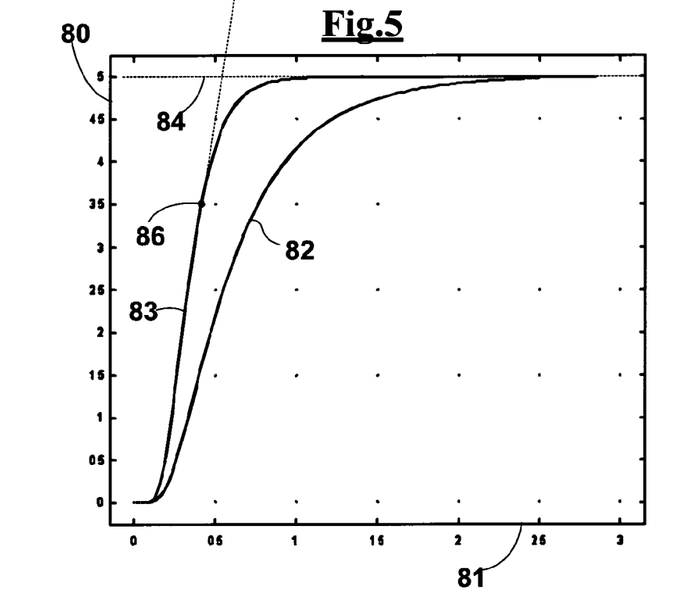
FIG. 5 shows a comparative diagram of the course of gas permeation obtained with the known systems relative to the present invention, where, after a first measuring step at a high pressure, the pressure is reduced to a value close to atmospheric pressure.

Normally, if the film has to be used for preserving products at atmospheric pressure, the process to measure permeation is normally performed at pressure that is close to atmospheric pressure. In the method according to the invention, reduces the pressure to a value that is close to atmospheric pressure so as to produce a permeation curve as shown in FIG. 5 where the prior art curve 82 represents the permeation course obtained with the known systems, whereas the permeation curve 83 represents the course obtained with the present invention. This curve 83 is obtained with a starting step of increasing the pressure to a high value and then reducing the pressure to atmospheric pressure starting from point 86. This method allows the system to obtain permeation curve 83 having a sample gas fraction that increases much more steeply than that of prior art curve 82 even if the actual measurements are performed at a pressure that is at or close to atmospheric pressure. The operation of the process with a transient phase starting at a high pressure provides a faster stabilization of the permeation measurements in a shorter time before the known systems.

Figure 6:
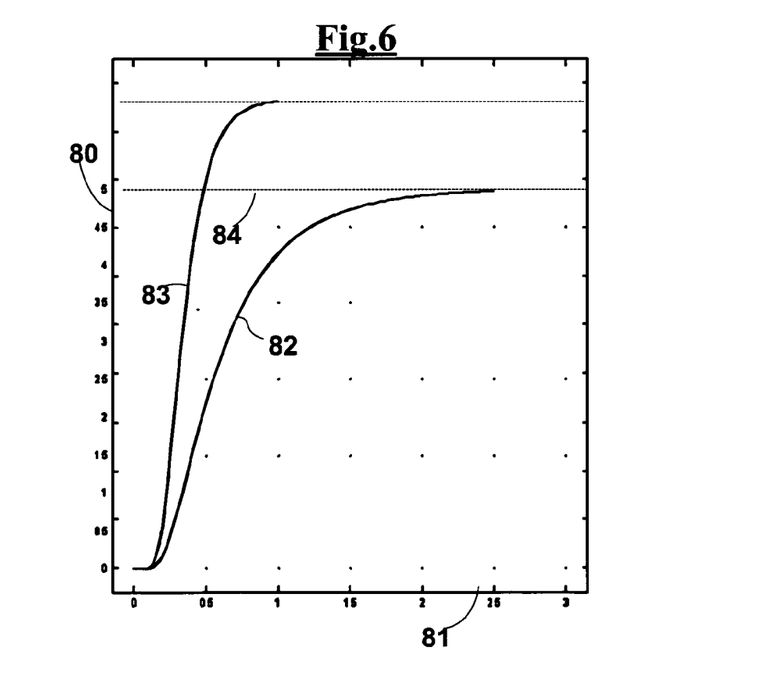
FIG. 6 shows a comparative diagram of the course of gas permeation obtained with the known systems relative to the present invention, wherein, after a first measuring step at a high pressure, the pressure is partially reduced but still at a pressure higher than atmospheric pressure.

FIG. 6 shows a further course 83 of the permeation measurement process according to the invention after a transient phase starting at a relatively high first pressure, this pressure is reduced to a second pressure that is less than that of FIG. 4 but higher than the atmospheric pressure. Inspection of FIG. 6 will show that superatmospheric pressure produces a permeation that is higher than the permeation orates shown in of FIG. 5.

Figure 7:
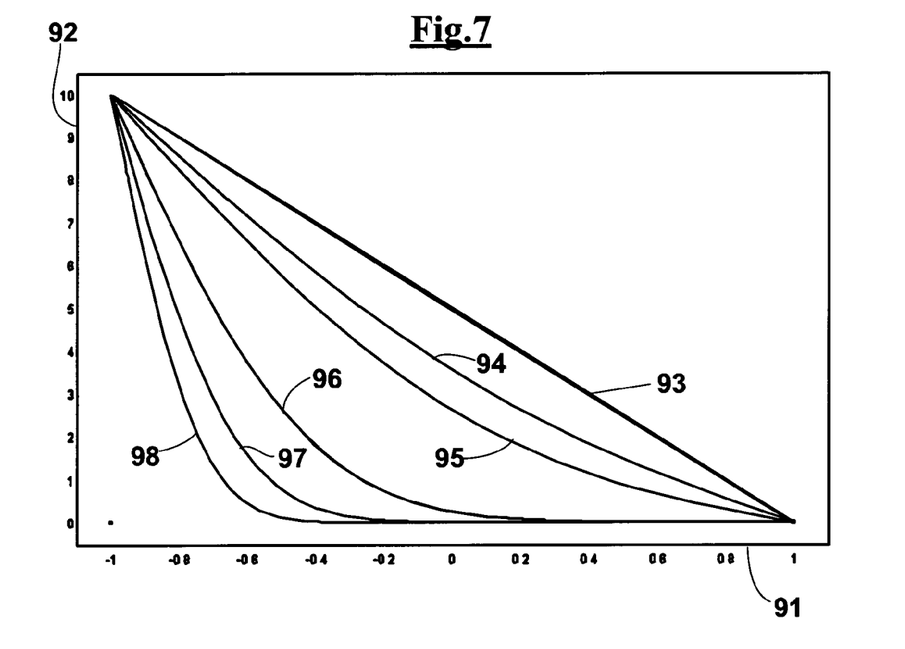
FIG. 7 shows a diagram that describes the time for developing a gas concentration in the thickness of the film according to the traditional technique.
Figure 8:
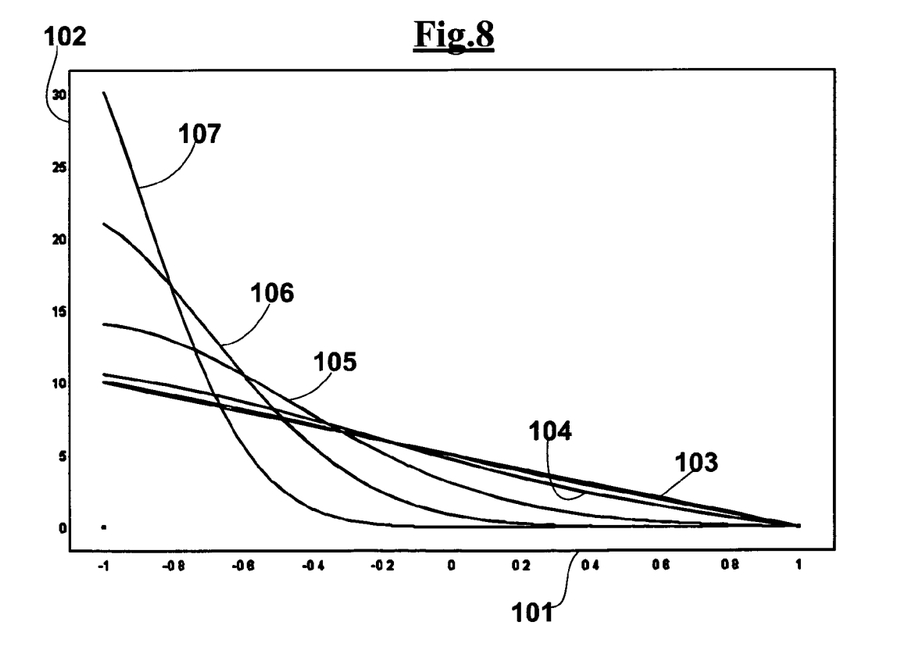
FIG. 8 is a further chart that illustrates the time to develop a gas concentration in the thickness of the film according to the present invention.

FIG. 7 shows the development time of the gas concentration found in the thickness of the test membrane using a known method, whereas FIG. 8 shows the corresponding development time that is obtained with the method according to the invention. The graphs in FIGS. 7 and 8 have in ordinate (92 or 102) the concentration of a gas in the film and in abscissas (91 or 101), the position of detection along the thickness of the film relative to the middle plane and expressed in fractions of the semi-thickness. The curves in FIGS. 7 and 8 reflect the differing concentrations of initial gas at various times in the process in both cases. In FIG. 7, curve 98 corresponds to a time of 0.04 hours, curve 97 to a time of 0.1 hours, curve 96 to a time of 0.2 hours, curve 95 to 0.4 hours, curve 94 to 0.6 hours and curve 93 to 2.0 hours.

In FIG. 8, curve 107 corresponds to a time of 0.04 hours, curve 106 to 0.1 hours, curve 105 to 0.2 hours, curve 104 to 0.4 hours, and curve 103 to 0.6 hours.

FIG. 7

| Ref. Curve | Time (Hrs.) | FIG. Ref. Curve |
|---|---|---|
| 98 | 0.04 | 107 |
| 97 | 0.1 | 106 |
| 96 | 0.2 | 105 |
| 95 | 0.4 | 104 |
| 94 | 0.6 | 103 |
| 93 | 2.0 | — |

The description of the above preferred specific example is presented to show the invention so that others in the art using the prior art knowledge, can change and/or adapt the invention in various applications without further research and without moving away from the inventive concept. It is intended that such adaptation and changes will be considered as equivalent of the exemplified method and device. The means and the material to provide the various functions described can be changed and modified without departing from the spirit and scope of invention. The expressions and terminology used herein are intended to have purely descriptive purposes and will not act as limiting the attached claims.

The invention claimed is:

1. A method for measuring permeability of a gas sample through a thin film or a wall, comprising the steps of:
   arranging said thin film or wall as a membrane between a first chamber and a second chamber in a sealed way, said membrane separating and sealing said first chamber and said second chamber;
   causing said gas sample to flow into and out of said first chamber causing a carrier gas to flow into and out of said second chamber, whereby an amount of said gas sample permeates into said second chamber through said membrane over a period of time and is conveyed away from said second chamber by said carrier gas;
   determining a rate at which said gas sample permeated into said second chamber and was present in the flow of said carrier gas exiting from said second chamber;
   characterized in that said steps of causing said gas sample and said carrier gas to flow are made at a total pressure of said gas sample and said carrier gas in said first and second chambers at a predetermined value which is higher than ambient pressure; while the total pressure difference between said first and second chamber remains substantially equal to zero.

2. A method, according to claim 1, whereby said total pressure predetermined value of the gas is set between 2 and 15 bar.

3. A method, according to claim 1, whereby a further step is provided of reducing said total pressure in said first chamber and said second chamber up to a value less than said predetermined value.

4. A method, according to claim 3, wherein said lower value is
   a value less than said first predetermined value but higher than the atmospheric pressure; or
   a value substantially equal to the atmospheric pressure.

5. A method, according to claim 3, whereby said step of reducing the total pressure is obtained by:
   controlling the total pressure in said first chamber and the total pressure in said first chamber and said second chamber with a feedback automatic control system based on the concentration of the gas sample present in the flow of carrier gas exiting from said second chamber; or
   controlling the total pressure in said first chamber and the total pressure in said first chamber and said second chamber with an open loop automatic variation programmed of the total pressures of said first and second chambers.

6. A method, according to claim 1, further comprising the step of cleaning said first chamber, said second chamber and said membrane, by passing a controlled flow of carrier gas through said first chamber and second chamber, whereby the total pressure difference between said first and second chamber is kept substantially equal to zero, and said total pressure has been increased up to a predetermined washing value that is higher than ambient pressure.

7. A device for measuring the permeability of a gas through a membrane of thin film or a wall, comprising:
   a first chamber and a second chamber each having, respectively, a first opening and a second opening that operatively face each other and are arranged at opposite sides of said membrane, said first and second opening being sealed against external surfaces of said membrane wherein a sample gas flows into and out of said first chamber and a carrier gas flows into and out of said second chamber whereby sample gas that permeates through the membrane into the second chamber flows with said carrier gas towards said outlet of said second chamber;
   characterized in that means are provided for measuring and adjusting the pressure in said first and second chamber said means being adapted to increase the total pressure of said gas sample and said carrier gas in said first and second chambers at a predetermined value which is higher than ambient pressure while the total pressure difference between said first and second chamber remains substantially equal to zero.

8. A device, according to claim 7, wherein said carrier gas consists essentially of:
   nitrogen;
   hydrogen;
   helium; or
   a mixture of nitrogen, hydrogen and helium.

9. A device, according to claim 7, wherein said gas sample is:
   oxygen; or
   carbon dioxide.

10. A device, according to claim 7, wherein said means for measuring and adjusting the pressure are also adapted to reduce said total pressure in said first chamber and said second chamber to a further total pressure predetermined value, that is not higher than said predetermined value.

11. A device, according to claim 7, wherein said first chamber is disposed in a first hollow object and said second chamber is disposed in a second hollow body, said second hollow body creating a base and said first hollow object creating a cover operatively engageable with said base, said membrane being arranged between said base and said cover.

12. A device, according to claim 11, wherein said cover is operatively pressed on said base by:
   at least one bracket;
   at least one screw;
   a screw threaded surface between said cover and said base;
   a fixed joint; or
   at least one element of engaging said cover to said base, coupled pivotally for rotation or slidingly with respect to said base.

13. A device, according to claim 11, wherein said first chamber and said second chamber each have a cylindrical shape.

14. A device, according to claim 7, wherein said means for measuring and adjusting the total pressure of gas in said first chamber and said second chamber is arranged upstream from said first chamber and said second chamber.

15. A device, according to claim 7, wherein said means for measuring and adjusting the flow is arranged downstream of said first chamber and said second chamber.

16. A device, according to claim 7, wherein said means for measuring the concentration of the gas exiting from said second chamber are arranged downstream of said second chamber.

17. A device, according to claim 7, further comprising means for adding humidity to said gas sample.

18. A device, according to claim 17, wherein said means for adding humidity comprises:
   an outer reservoir containing a liquid and having an inlet and an outlet that allows for a flow of said gas sample through said reservoir;

at least one inlet duct arranged upstream from said reservoir and exiting into said inlet and at least one delivery duct arranged downstream of said reservoir, whereby said delivery duct exits into said first chamber.

19. A device, according to claim 18, wherein said inlet duct of said reservoir comprises a valve adapted to switch the flow of said gas sample between said inlet duct of said reservoir and said inlet of said first chamber.

20. A device, according to claim 7, further comprising means for measuring the humidity of said gas sample and is arranged downstream of said outlet of said first chamber.

21. A device for measuring the permeability of a gas through a membrane of thin film or a wall, said device comprising:

a sample gas flow line;

a carrier gas flow line;

a first chamber and a second chamber having, respectively, a first opening and a second opening that operatively face each other and that are arranged on opposite sides of said membrane so that said first opening and second opening are sealed against an outer perimeter of said membrane, each of said first chamber and said second chamber having at least one inlet and one outlet whereby a sample gas from said sample gas flow line enters and then exits said first chamber and a carrier gas from said carrier gas flow line enters and then exits from said second chamber so that sample gas from said first chamber that permeates through the membrane into the second chamber will flow with said carrier gas towards the outlet of said second chamber; and a flow regulator, a pressure regulator and an associated control unit for each of the sample gas line and carrier gas line that control the pressure in said first chamber and said second chamber.

* * * * *